US006180340B1

(12) United States Patent
Nelson

(10) Patent No.: US 6,180,340 B1
(45) Date of Patent: Jan. 30, 2001

(54) EXTENDED DYNAMIC RANGE ASSAYS

(75) Inventor: Norman C. Nelson, San Diego, CA (US)

(73) Assignee: Gen-Probe Incorporated, San Diego, CA (US)

( * ) Notice: Under 35 U.S.C. 154(b), the term of this patent shall be extended for 0 days.

(21) Appl. No.: 08/962,033

(22) Filed: Oct. 31, 1997

(51) Int. Cl.[7] .................... G01N 33/533; G01N 33/53
(52) U.S. Cl. ............... 435/6; 435/7.1; 435/7.21; 435/7.4; 435/7.5; 435/7.7; 435/7.9; 435/7.91; 435/962; 435/968; 436/537; 436/544; 436/545; 436/546; 436/800; 436/814; 436/815; 436/817
(58) Field of Search ................ 435/6, 7.1, 7.4, 435/7.5, 7.7, 7.9, 7.91, 962, 968, 7.21; 436/544–546, 537, 800, 814, 817, 815

(56) References Cited

U.S. PATENT DOCUMENTS

| 4,486,530 | * | 12/1984 | David et al. ................ 436/519 |
| 4,514,505 | * | 4/1985 | Canfield et al. ............. 435/962 |
| 4,595,661 | | 6/1986 | Cragle et al. ............... 436/534 |
| 4,946,958 | | 8/1990 | Campbell et al. . | |
| 5,283,174 | | 2/1994 | Arnold, Jr. et al. . | |
| 5,639,604 | | 6/1997 | Arnold, Jr. et al. . | |
| 5,656,207 | | 8/1997 | Woodhead et al. . | |
| 5,656,744 | | 8/1997 | Arnold, Jr. et al. . | |
| 5,658,737 | | 8/1997 | Nelson et al. . | |
| 5,710,029 | | 1/1998 | Ryder et al. . | |
| 5,739,042 | * | 4/1998 | Frengen ...................... 435/962 |

FOREIGN PATENT DOCUMENTS

| 1 185 177 | * | 4/1986 | (CA) .................. 435/962 |
| 0 114 668 A2 | * | 8/1984 | (EP) . | |
| 0 709 466 A2 | * | 5/1996 | (EP) . | |
| 0747488 | | 12/1996 | (EP) . | |
| 0747706 | | 12/1996 | (EP) . | |
| 8911101 | | 11/1989 | (WO) ................... 33/546 |
| 9100511 | | 6/1990 | (WO) . | |
| 9517674 | | 6/1995 | (WO) ................... 33/543 |
| 9517675 | | 6/1995 | (WO) ................... 33/546 |
| 9641178 | | 5/1996 | (WO) . | |

OTHER PUBLICATIONS

K. Van Dyke et al, ed., B. Terouanne et al, "Direct Bioluminescent Immunoassays of Proteins and Haptens" in Luminescence Immunoassay and Molecular Applications (CRC Press, Inc., Boca Raton, FL 1990), pp. 179–185.*

Nelson, et al., "Detection of Acridinium Esters by Chemiluminescence" in Non–Isotopic Probe Techniques, pp. 275–310, 1992, Larry J. Kricka, ed., Academic Press 1992.

Weeks, et al., "Acridinium Esters as High–Specific–Activity Labels in Immunoassay", Clin. Chem., 29(8):1474–1479 (1983).

* cited by examiner

*Primary Examiner*—Mary E. Ceperley
(74) *Attorney, Agent, or Firm*—Christine A. Gritzmacher; Carlos A. Fisher

(57) ABSTRACT

A method and compositions for the detection and/or quantification of an analyte through the use of a plurality of labeled probes, with two or more said probes targeted to different regions of said analyte. In specific embodiments, the labels are separately distinguishable, and/or are present at different specific activities on the labels.

44 Claims, 7 Drawing Sheets

EXTENDED DYNAMIC RANGE ASSAYS

FIELD OF THE INVENTION

This invention concerns compositions and methods for the detection of analytes which may be present in a wide range of possible concentrations through the use of two or more labeled binding partners. In a particular embodiment, two or more separately distinguishable labels are each joined to binding partners designed to bind two mutually exclusive target regions of the same analyte. In this preferred embodiment, the label joined to each said binding partner is present at a different specific activity. In other embodiments, the labels are present on the binding partners at the same specific activity, or are not separately distinguishable. The present invention provides for the extension of the dynamic range of any assay to be used for detection of any analyte, using any label type or combination of label types. The binding partners must be able to bind the analyte in a target region-specific manner; otherwise the binding partners may be of any type. The invention is useful in any application in which the detection of analyte is desired: these include, without limitation, nucleic acid hybridization assays, antibody binding assays, enzyme-substrate interactions, cytokine-receptor interactions, hapten-ligand interactions, and the like.

BACKGROUND OF THE INVENTION

Assays for the detection and/or quantification of analytes exist in many different forms and formats. In many cases, the amount of the analyte sought to be detected in a sample is not great enough for direct detection or quantification. In such cases, a secondary molecule able to bind to or interact with the analyte must be used to indicate the presence or amount of analyte in a given sample. Unless the secondary molecule is directly detectable, the secondary molecule must be conjugated with a label which will be detected when the secondary molecule binds the analyte. For the purposes of the present application, such secondary molecules able to bind or interact with analytes will be referred to as "binding partners" or "probes". A non-exclusive list of analytes sought to be detected are antibodies, proteins, cell-surface receptors, cytokines, hormones, antigens, nucleic acids, metals, molecular complexes such as polymeric arrangements of proteins or other macromolecules, and the like. Likewise, binding partners for the detection of such analytes may include, without limitation: antibodies, proteins, antigens, haptens, nucleic acid probes, chelating agents, enzymes, enzyme substrates, and analogs of these.

One commonly used assay format is the enzyme-linked immuno-absorption assay (ELISA). In this assay format the analyte is contacted with a primary antibody able to bind at least one domain or "target region" thereon. After the excess antibody is washed free of the resulting analyte: antibody complex, the primary antibody is contact with an enzyme-labeled secondary antibody to which it will specifically bind. The sample is then given a chromogenic enzyme substrate, and incubated under conditions favoring enzyme-mediated reaction of the substrate. The resulting colored product and its intensity after a given reaction time are indications of the presence and amount, respectively, of the analyte originally present in the sample. Illustrative examples of enzymes used in such assay methods are β-galactosidase, acid phosphatase, and alkaline phosphatase; a non-exhaustive list of enzyme substrates for use with such enzymes include x-gal (5-bromo-4-chloro-3-indolyl-β-D-galacto-pyranoside) and p-nitrophenyl phosphate. Other such enzymes and substrates are well known by those of skill in the art. Variations of this assay method exist; for example, the primary antibody may be linked to an enzyme thus eliminating the secondary antibody step. Nevertheless, these assay methods feature common steps involving contacting of the analyte with a labeled binding partner and subsequent detection of the analyte-bound label as an indication of the presence or amount of analyte.

While ELISA utilizes an enzyme label which is indirectly detected, other methods exist for the direct detection of labeled binding partner. Thus, Campbell, et al., U.S. Pat. No. 4,496,958 describes chemiluminescent acridinium labeling compounds for use in labeling binding partners in multiple assay formats; this patent is incorporated by reference as part of the present application. Additionally, other labeling compounds such as radionuclides, fluorescent, bioluminescent, phosphorescent, luminescent, chemiluminescent, or electrochemiluminescent compounds, chromophores, and dyes are known in the art and are commonly used as labeling agents in a variety of assay formats, both direct and indirect, including immunoassay and nucleic acid hybridization assays.

In addition to distinctions between assays based on the type of analytes to be detected, the type of binding partner with which the analyte binds, and the type of label used, assays can also be classified according to whether the method involves the immobilization of the analyte, or the analyte: binding partner complex. In the most common assay format, known as a "heterogeneous" or biphasic assay system, a probe is allowed to bind its analyte—usually under conditions of probe excess. Either the analyte molecule or the probe molecule may be immobilized to a solid support, thus causing the resulting probe: analyte complex to become immobilized—alternatively, and preferably, the complex may be immobilized following its formation in the liquid phase. After probe: analyte complexes have been immobilized, the excess uncomplexed probe molecules are washed away. If the probe molecules are directly labeled, the label may now be detected as an indication of the presence of analyte. In a variation of this format, probe analyte complexes may also be separated from free probe, by means such as gel filtration chromatography, electrophoresis, electrofocusing, and other separation methods based on size or charge of the probe: analyte complex.

Alternatively, and more rarely, an assay may be designed to take place wholly in a single phase without a step resulting in the physical separation of probe: analyte complex from free probe. Such assay methods are termed "homogeneous" assays. In such methods, usually either the analyte: probe complex, or the free probe is altered after formation of the complex to permit the separate detection of analyte in the presence of the free probe. One such way of differentiating free probe from probe-bound analyte involves alteration or selective inactivation of the label joined to the probe rather than the free probe molecule itself. Arnold, et al., U.S. Pat. No. 5,283,174, describes homogeneous methods employing a oligonucleotide probe joined to a label which is capable of selective inactivation or alteration based on whether the labeled probe is bound to its target or not. These methods may be used in a single tube without the need for washing or decanting. This patent enjoys common ownership with the present application, and is incorporated by reference herein.

Assay methods exist which may utilize aspects of both homogeneous and heterogeneous assays. These methods may, for example, employ a single phase selective alteration of the probe or the probe: analyte complex followed by a physical separation step to further decrease the level of background in the assay. Such a "hybrid" assay format is described as one aspect of the multiple analyte assay described in Nelson et al., U.S. Pat. No. 5,658,737 which is incorporated by reference herein.

Regardless of the assay format used, a number of factors exist in all assays which can limit their sensitivity and the range of possible analyte concentrations that can be accurately detected or measured. One such factor is the level of background present in the assay. "Background" is a term used to describe probe or label in the assay which is not bound specifically to analyte and which may mask positive results at low analyte levels. Thus, for example, in a heterogeneous assay, background may be provided by a small amount of probe which is not removed during the physical separation of probe: analyte complex from free probe. If the probe is labeled, this small amount of probe will be detected as a residual level of detectable signal. In a homogeneous assay, background may be provided by the inability to totally alter all free probe or, probe-linked label molecules. In either case, a small level of signal, commonly between 0.001% and 10% of the total signal, more commonly between about 0.01% and 1%, is present as a "baseline" below which results cannot be relied on for accuracy. Thus, the level of background inherent in a particular assay format limits the lowest amount of analyte which can be detected and/or measured.

The phenomenon of residual background in an assay plays a part in limiting the "dynamic range" of that particular assay. By "dynamic range" is meant a linear or predictably accurate correspondence between the level of analyte present in the sample to be assayed and the amount of signal obtained from the label used to indicate the analyte's presence. It is readily apparent to those of skill in the art that the dynamic range of an assay cannot extend below the level of background contributed by the detection of non-specific label, thus the higher the background, the more the dynamic range is limited. Moreover, if high amounts of analyte are to be detected, correspondingly high amounts of probe have to be used, which leads to higher backgrounds.

Other factors may contribute to limitations on the extent of a particular assay's dynamic range. A major additional factor is often the maximum amount of signal able to be read or reported by the label detection device or instrument to be used in the assay. Thus, if a given instrument can only accurately read up to, for example, one million counts per second and the sample yields 2 million counts per second, the extra one million counts are not being reported by the instrument, and the upper extent of the assay dynamic range is half of what is necessary to accurately quantify the sample.

Additionally, instruments used to detect the labeled probe: analyte complexes may have inherent electronic "noise", which is also commonly termed "background", and which can also contribute to limitations on the accuracy of the detection of the analyte. While improvements to, and optimization of an instrument's electronic signal-to-noise ratio are possible, the noise obtained in a specific instrument combines with the inherent assay background described above to further limit the ability to detect or quantify analytes across a wide range of possible concentrations. In order to overcome these limitations, it is currently necessary for workers to obtain multiple samples from a single source, or to make serial dilutions of a sample to test for the presence of an unknown amount of analyte.

There is, therefore, currently a need in the art for methods and compositions for detecting and/or quantifying analytes of every kind in a single tube without the need for sample dilutions or duplicate samples. Preferably, such methods and compositions would involve a single addition of detection probes from which possible analyte concentrations differing by orders of magnitude can be detected. Such methods should also generally be independent of the analyte type, probe type, label type, and instrument to be used for the detection of analyte.

SUMMARY OF THE INVENTION

The present invention is directed to methods and compositions permitting the detection of at least one analyte over a broader total concentration range than is otherwise commonly possible. In its most basic form, the invention utilizes two or more labeled probes, each probe targeted to the same analyte in a different target region. Each labeled probe is used to detect analyte within a different specified concentration range, and is present in the assay in an amount which corresponds in a defined manner to the maximum molar amount of analyte within that range. Thus, the labeled probe molecules are present in the assay at different concentrations, which correspond to the different analyte concentration ranges sought to be detected. In an embodiment of the invention, the signal produced by each of the labels can be indistinguishable; however, in a preferred embodiment the signal produced by each label is independently distinguishable. Furthermore, each probe may be labeled at the same, or preferably at different specific activities.

Thus, in a first aspect, the invention concerns a method of detecting analytes and extending the range of concentrations at which said analytes can be detected, by using two or more probe molecules labeled with a detectable label. Each probe molecule is directed to a different target region of the same analyte.

Preferably, the labels to which the probe molecules are joined are separately detectable. By "separately detectable" is meant that the labels can be present in the same reaction vessel and each distinguished in the presence of the other. Such labels may be of the same general type, such as radionuclides (for example, $^{32}P$ and $^{125}I$; the first being detectable by emission of $\beta$ particles and the other by emission of $\gamma$ rays), and different chemiluminescent or fluorescent labels. Alternatively, one probe may be labeled with a particular type of label and another probe may be labeled with a different type of label, such as the first with a radionuclide and the second with a fluorescent label. In less preferred embodiments the labels used to "tag" the probes need not be separately detectable so long as they are present on each probe at different specific activities.

By "labeled" is meant that a probe is joined to a labeling compound. The label can be joined either directly or indirectly. An example of indirect labeling is through the use of a bridging molecule, such as a secondary antibody or a bridging oligonucleotide, which is itself either directly or indirectly labeled. Direct labeling can occur through covalent bond formation or through non-covalent interactions such as hydrogen bonding, hydrophobic and ionic interactions, or through the formation of chelates or coordination complexes.

When reference is made to the concentration or amount of a particular probe corresponding to an amount of analyte which the probe is designed to detect, it will be understood that by "corresponding to" is meant that the concentrations or amounts of the probe and analyte are related in a predictable and reproducible way; for example, by a given ratio, under a given set of assay conditions.

By "oligonucleotide" is meant a multimeric compound comprised of nucleosides or nucleoside analogs which have nitrogenous bases, or base analogs, able to specifically bind a nucleic acid analyte to form a stable probe:analyte complex. The nucleosides may be linked together by phosphodiester bonds to form a polynucleotide, or may be linked in any other manner that permits the formation of a target-specific complex with a target nucleic acid. Other internucleoside linkages may include phosphorothioate linkages, methylphosphonate linkages, and peptide bonds. Peptide nucleic acids are defined herein as oligonucleotides. Sugar moieties may be substituted with groups affecting stability of the hybridization reaction (but not extinguishing formation of a target:probe complex), as, for example, with 2' methoxy substitutions and 2' halide substitutions such as 2'-F. Similarly, while the bases may consist of the "traditional" bases adenine, guanine, cytosine, uracil and thymine, analogs of these bases are well known in the art, (see, e.g., *The Biochemistry of the Nucleic Acids* 5–36 (Adams et al., ed. 11$^{th}$ ed. 1992), which is hereby incorporated by reference herein), and are contemplated to be within the scope of this term.

By "specific activity" is meant units of detectable signal obtained from a label per unit measurement of probe. The units of detectable signal may be expressed in counts per minute (cpm), light absorbance units at a given wavelength, relative light units (rlu), units of enzymatic activity or any other unit of measuring the amount of label present. Likewise, the units of probe measurement may be expressed as units of mass, such as $\mu$g, or as a measurement of the number of molecules of probe, such as $\mu$moles.

By the terms "binding partners" or "probes" is meant a molecule able to bind to or interact with the analyte. A probe or binding partner is used to indicate the presence or amount of analyte in a given sample. Unless the probe or binding partner is directly detectable, the probe is directly or indirectly conjugated with a label. A non-exclusive list of analytes which may be sought to be detected are antibodies, proteins, enzymes, lipids, carbohydrates, cell-surface receptors, cytokines, hormones, antigens, nucleic acids, metals, molecular complexes such as polymeric arrangements of proteins or other macromolecules, and the like. Likewise, binding partners for the detection of such analytes may include antibodies, antigens, haptens, nucleic acid probes, chelating agents, enzymes, enzyme substrates, proteins and analogs of these.

By "target region" or "region" is meant any portion of an analyte, continuous or discontinuous, which binds to a given probe (or binding partner) or class of probes. For example, without limitation, when the analyte is a nucleic acid molecule, a target region may comprise a nucleotide base sequence which will specifically bind a probe. The target region may also comprise a particular secondary or tertiary structure of the target analyte to which a probe is directed. If the analyte is a protein or peptide, the target region may be an amino acid sequence or a conformational domain within the protein or peptide that can bind to a probe. Preferably, each target region does not overlap any other target region of the same analyte, so that simultaneous application of each probe to the analyte will not produce competition between probes.

It is also, therefore, an object of the invention to provide methods for the detection of a wide range of target analyte concentrations. Typically, these methods can increase the ability to accurately detect the analyte by at least two orders of magnitude; however through the use of additional probes and separately distinguishable labels, the Applicant contemplates that the dynamic range of an assay may be extended by 3–6 orders of magnitude or more. Such methods allow the detection of analyte in a sample without the need to perform sample dilutions or to test replicate samples under different conditions. This is possible since according to the present invention, the dynamic response of the assay to expected analyte levels is designed a priori to cover desired ranges of analyte amounts. Thus, preferred aspects of the invention provide a method for the analysis of a sample in a single tube.

It is further an object of the present invention to provide compositions for the detection or quantification of an analyte that can be used by a person with a minimum of specialized training in medical, clinical, or scientific methodology. By permitting the testing of an analyte which may be present in a sample at a concentration anywhere within a wide range of potential concentrations, the invention provides compositions which can permit the automation of many aspects of diagnostic assays while minimizing sample handling and the attendant heightened risk of error. Thus, the present invention provides useful means for minimizing the level of specialized training necessary for laboratory personnel to conduct assays, while permitting such assays to be easily automated with reduced variability of results.

A further object of the present invention is to provide a method for detecting or measuring one or more analyte suspected of being present in a sample comprising the steps:

a) contacting
  i) said sample, and
  ii) a probe reagent comprising two or more probes, each said two or more probes joined to a label and able to selectively bind to a separate target region of said analyte, wherein each said labeled probe is designed to detect said analyte over a different range of analyte concentrations and wherein the amount of each said probe present in said probe reagent corresponds to the amount of said analyte sought to be detected by that probe, under conditions favoring the binding of said probe molecules with said analyte, if present, and b) detecting the presence of at least one said label as an indication of the presence or amount of said analyte in said sample, wherein the range of possible analyte amounts in said sample able to be detected or measured by said probe reagent is greater than the range of analyte amounts in said sample able to be detected or measured by any one said labeled probe, and wherein both said contacting and detecting steps are capable of being performed in the same vessel. In this embodiment, the invention may comprise the use of separately distinguishable labels. Additionally, and independently, the invention may comprise the use of two or more labeled probes having different specific activities.

Probes are present in the probe reagent in different amounts. The amount of each probe corresponds to and defines the upper limit of the range of analyte concentrations which that labeled probe is designed to detect. This is a greatly preferred feature of the invention, since the amount of each labeled probe in the assay can define the amount of background present. Additionally, when the probes differ in their specific activities, the probe having the highest specific activity is generally present in the lowest amount, while the probe having the lowest specific activity is generally present in the highest amount. In this way, background levels from label associated with unbound probe are minimized.

It is yet further an object of the invention to provide compositions and kits for detecting analytes which may be present in a sample within a wide range of possible concentrations. Such compositions may be drawn to a probe reagent comprising two or more probes, each probe being joined to a label and designed to bind to a separate target region of said analyte, wherein each said labeled probe is designed to detect said analyte over a different range of possible analyte concentrations and wherein the concentration of each said probe present in the reagent corresponds to the concentration the analyte sought to be detected.

In each of these embodiments, the analyte may comprise any molecule or complex capable of binding two or more probes. Likewise, a probe may comprise any molecule capable of specifically binding to a target region of the analyte. Each of the probe and the analyte may comprise compounds including an antigen, an antibody, a hormone, a protein, a cytokine, an oligonucleotide, a cellular receptor, a nucleic acid, and a peptide nucleic acid.

BRIEF DESCRIPTION OF THE DRAWINGS

in FIG. 1A, standard AE, naphthyl-AE, ortho-AE ("o-AE"), 1- or 3-methyl-AE ("1 or 3-Me-AE"), 2,7-dimethyl-AE ("2,7-diMe-AE"), and 4,5-dimethyl-AE ("4,5-diMe-AE"); in FIG. 1B, ortho-dibromo-AE ("o-diBr-AE"), ortho-dimethyl-AE ("o-diMe-AE"), meta-dimethyl-AE ("m-diMe-AE"), ortho-methoxy-AE ("o-MeO-AE"), ortho-methoxy(cinnamyl)-AE ("o-MeO(cinnamyl)-AE"), and ortho-methyl-AE ("o-Me-AE"); and in FIG. 1C, ortho-fluoro-AE ("o-F-AE"), 1- or 3-methyl-ortho-fluoro-AE ("1 or 3-Me-o-F-AE") and 1- or 3-methyl-meta-difluoro-AE ("1 or 3-Me-m-diF-AE").

FIG. 3A shows the chemiluminescent signal obtained from o-F-AE-labeled Probe 1 as a function of target amount. FIG. 3B shows chemiluminescent signal obtained from 2-Methyl-AE-labeled (2-Me-AE-labeled) Probe 2 (present at a specific activity 100-fold less than that of the o-F-AE-labeled Probe 1), also as a function of target amount.

DETAILED DESCRIPTION OF THE INVENTION

Figure 1A:
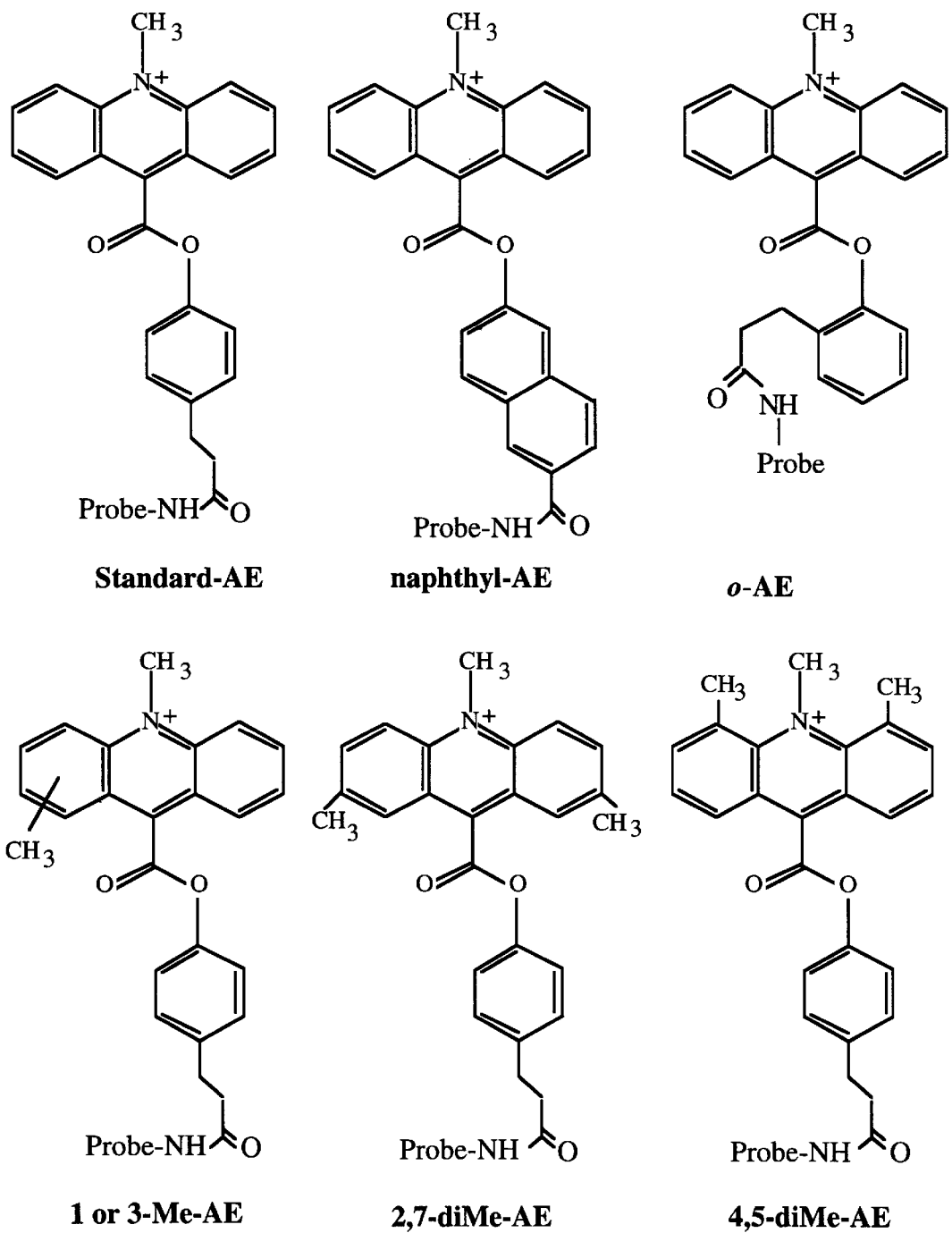
FIGS. 1A, 1B and 1C show the structure of a number of acridinium ester ("AE") derivatives, and their corresponding nomenclatures, which have different chemiluminescent reaction kinetics or wavelengths of light emission such that certain combinations of these labels may be used as distinguishable labels in the present invention. The chemical compounds shown, attached to a "Probe" via an amide linkage are.

The Applicant has invented methods, kits, and compositions for the detection and measurement of an analyte which may be present in a sample within a wide range of concentrations. This method obviates the need to dilute samples or make replicate tests of a single sample under different conditions, as has previously been required. The invention is therefore useful in providing a cost-, time-, and labor-effective format for the detection of any given analyte capable of binding two or more binding partners.

By way of illustration, and not of limitation, the invention involves three observations. The first such observation is that any assay system employing a label for detection of an analyte yields a certain background level of non-specific signal contributed by "free" label. By "free" label is meant label that is present in the assay in an unbound form after the assay has been performed, or label joined to probe molecules that have failed to bind analyte and which yields detectable signal upon detection. Each assay format typically has a certain inherent background level; while this amount may vary from assay to assay, it is typically in the range of about 0.01% to about 10%, or more preferably in the range of about 0.01% to about 1%, of the total signal which can be accurately measured in the assay. Background can also be contributed by the electronic noise present in the instrument used to detect the label.

The second observation is that each instrument or method used to detect label has a certain "maximum" level of signal detection, beyond which additional signal is not detected. For example, a luminometer may have a maximum detection level of 2 million relative light units (rlu). If a sample containing label amounting to 4 million rlu is read in this instrument, the instrument will underestimate the amount of label present in the sample by half, since it will indicate that 2 million rlu are present; this is described as loss of dynamic range at the "top end". When this finding is combined with the first observation, it can be readily seen that there are limits on both the minimum and the maximum levels of analyte detectable in a standard assay system.

The third observation is that certain different labels are able to be detected separately in the presence of each other. Thus, the background contributed by a first such label will not usually substantially interfere with the detection of any other label, so long as such other labels may be detected independently of the first label. Although it is advantageous if the labels are detected with no interference from other labels, in the currently preferred embodiment some such insubstantial interference may occur without posing a significant problem or preventing independent detection of the labels.

Background contributed by labeled probes poses a problem when different probes cannot be distinguished at all. The background contributed by one probe, when present in high amounts, will obscure low amounts of signal from a probe present in low amounts. This situation can be solved in two ways. First, probes can be used having different specific activities; thus the labeled probe present in high amounts will not create too high a background if its specific activity is low. Second, even if the probes have the same specific activity, if they are independently discernable, the background contributed by one labeled probe will not overwhelm the signal obtained by a probe present in low amounts.

When populations of different probe molecules are each targeted to separate target regions of a single analyte, the different probes will not compete with each other for binding and thus they constitute separable indications of the presence of the analyte. When the probe molecules are labeled, the separate detection of each target region is possible with each target region being an independent indication of the presence of the analyte. By supplying each labeled probe at a different concentration from each other labeled probe, each target region will be an indication of a range of possible analyte concentrations. Thus, a collection of such probes constitutes a "ladder" of concentration ranges which can be detected.

In its most basic form the present invention employs three similar but different methods which are capable of expanding the range of an assay. In order to more fully illustrate the invention, the following examples are provided. Examples 1–5 are hypothetical analyses of different aspects of the invention. Example 6 is an example demonstrating application of the invention. These examples are not intended to limit the scope of the invention, which is defined solely by the claims.

EXAMPLE 1

Indistinguishable Label, Different Specific Activities

In the first situation it shall be assumed for the purposes of this illustration that three probes are to be used, each targeted to different target regions of the analyte. It will be understood that any number of probes greater than one would be equally applicable in a given application of the invention. Each probe is labeled with a single type of label—in practice, this label could be different from probe to probe, such as different radionuclides or different fluorescent molecules, but the signal given off by each label is presumed to be indistinguishable from the signal given off by the other labels.

In the following examples, it will also be assumed that each probe is targeted to a target region which is present in only a single copy for each unit of analyte, e.g., a nucleotide sequence region unique to a target nucleic acid or a domain unique to a target polypeptide. However, the skilled worker will realize that a plurality of such sites may exist for each target region to which a particular probe is designed to bind. Thus, although the calculations which follow assume a one-to-one correspondence between target regions and analyte, in a case where two or more such target regions are present for each unit of analyte these calculations would differ only in requiring a simple correction to account for this fact.

Assume that analyte in the amounts from 0.01 fmole (1 fmole equals $10^{-15}$ moles) to 10,000 fmoles is sought to be detected. In such a case 1 fmole of probe 1, 100 fmoles of probe 2, and 10,000 fmoles of probe 3 could be used in the assay. The probes are labeled at different specific activities inversely related to the amount of probe in the assay; thus, assume that probe 1 is labeled at $10^8$ units of label/pmole ($10^{-12}$ moles) of probe, probe 2 with $10^6$/pmole and probe 3 with $10^4$/pmole. This results in the same amount of label being contributed by each probe: $10^5$ units.

When no analyte is present in the system assume that there is a background of 0.1% of the total detectable signal in the assay; this amount would then be 0.1%×$10^5$ units=100 units of background for each probe, and a total of 300 units for all three probes. This amount of background is quite low, as will be recognized by the skilled artisan, and permits the sensitive detection of analyte at a low concentration.

For example, if 3 attomoles (1 attomole equals $10^{-18}$ moles) of the analyte is present in the assay system, 3 attomoles of probe 1 will bind, and when the probe:analyte complex is separated from the unbound labeled probe it will produce a signal of 300 units. When this is combined with the assay background, the overall signal detected will be 600 units (300 contributed by background and 300 from probe 1), yielding a two-fold signal-to-noise (S/N) ratio at this analyte concentration; a two-fold S/N ratio or greater is generally accepted by those of skill in the art to represent a true positive signal.

When 3 attomoles of analyte is present, 3 attomoles each of probe 2 and 3 will also bind the analyte. However, due to their low specific activities, probe 2 will contribute only 0.3 units of signal, while probe 3 will contribute 0.0003 units; the signal from these probes will therefore not contribute to the signal obtained from probe 1 at this concentration of analyte.

If the concentration of analyte is increased to 1 fmole, all of probe 1 will bind to the analyte, and when the probe:analyte complex is separated from unbound labeled probe, all of the $10^5$ units of label will be detected; 0.1% of $10^5$ units of signal from probe 1 (100 units) is background in the assay. At the same time, 1 fmole of probes 2 and 3 will also have bound to the analyte; since these probes are labeled at a lower specific activity only 1000 units of the probe 2 label are detected and 10 units of the label joined to probe 3 is detected. The former is approximately only 1% of the total counts and the latter is below background. The total number of counts when 1 fmole of analyte is present is 100,000+1000+10=101,010 units.

When between 1 and 100 fmole of analyte is present, the detectable signal from probe 2 varies in proportion to target concentration. At such concentrations, all of probe 1 will have bound to its target region, and therefore its 100,000 units of label continue to be detected. However, now the label attached to probe 2 is also detected. At 100 fmoles of analyte, all of the available probe 2 has bound, and the probe 2 label is detected as another 100,000 units of signal. 100 fmoles of probe 3 has also bound at this concentration, contributing 1000 units of label; thus the 100 fmoles of label is detected as 100,000+100,000+1000=201,000 units of detectable signal.

Similarly, in the range from 100 fmoles to 10,000 fmoles of analyte, all of the available probe 1 and probe 2 in the reaction mixture has bound the analyte; thus 100,000 units of detectable signal has been obtained from each. Probe three is available to bind with up to 10,000 fmoles of analyte. When 10,000 fmoles of analyte are present, probes 1, 2, and 3 each contribute 100,000 units of detectable signal. Thus 10,000 fmoles (10 pmoles) of analyte is detected as 300,000 units of detectable signal. This scheme is shown in Table 1 below.

TABLE 1

| Amount of Target to be Detected (pmoles) | Probe 1 (units of signal) | Probe 2 (units of signal) | Probe 3 (units of signal) | Total Units of signal |
| --- | --- | --- | --- | --- |
| 0.00001 | 1,000 | 10 | 0.1 | 1,010.1 |
| 0.0001 | 10,000 | 100 | 1 | 1,011 |
| 0.001 | 100,000 | 1,000 | 10 | 101,010 |
| 0.01 | 100,000 | 10,000 | 100 | 110,100 |
| 0.1 | 100,000 | 100,000 | 1,000 | 201,000 |
| 1 | 100,000 | 100,000 | 10,000 | 210,000 |
| 10 | 100,000 | 100,000 | 100,000 | 300,000 |

It can be seen that the use of three different probes will extend the assay's range beyond that available using only one probe. This would not be true if the three probes were identical or otherwise targeted to the same target region of the analyte; in this case, since each probe would compete for binding with each other probe, the mixture of such probes would essentially constitute an "averaging" of the specific activities of the three probe species, with the higher abundance, low specific activity probe predominating.

EXAMPLE 2

Distinguishable Labels, Same Specific Activity

In the second embodiment, as in the first, three probes are used to detect three different target sites of a single analyte. For the purposes of this example, each probe is assumed to be labeled with a different, separately distinguishable label. In this example further assume that the probes are labeled at the same specific activity: hypothetically, $10^8$ units of label per pmole of probe. It should be kept in mind that these labels may be of the same or of different types: for example, all the labels may be chemiluminescent labels, or alternatively, one label might be a radioactive label, one a fluorescent label, and one a chemiluminescent label.

The same range of possible analyte concentrations is sought to be detected as in Example 1. Also as before, the probes are present in different amounts to correlate with the different analyte subranges for which each probe is to be used. Thus, 1 fmole of probe 1 is present, 100 fmoles of probe 2 is present, and 10,000 fmoles of probe 3 is present; since each probe is labeled at the same specific activity, there will be $10^5$ units of detectable label from labeled probe 1, $10^7$ units of detectable label from labeled probe 2, and $10^9$ units of detectable label from labeled probe 3 in the reaction mix.

Also, assume again that there is a background of 0.1% of the maximum detectable signal inherent in the assay. However, unlike Example 1, the labels are distinguishable in this assay. Thus, when 1 fmole of analyte is present all of probe 1 will bind to the analyte and will be detected as $10^5$ units of signal from probe 1; the background for probe 1 will be 100 units of signal. At this same analyte concentration, 1 fmole of probes 2 and 3 will also bind to the target, along with $10^5$ units of signal from each of their labels. However, since the labels are independently detectable, neither probe 2 or 3 will be detected when probe 1 is specifically detected. Nor will the background contributed by labels 2 and 3 usually affect the detection of label 1, or vice versa.

At amounts above 1 fmole of analyte, no additional probe 1 will bind, since only 1 fmole of probe 1 is present in the reaction mixture. Thus, when analyte is present at an amount of 100 fmoles (0.1 pmole), all of the added probe 1 is saturated with analyte; while 100 fmoles of probes 2 and 3 have bound to their respective target regions. At this point $10^5$ units of signal from probe 1 and $10^7$ units of signal from each probe 2 and probe 3 are detected; background from each of the labels associated with probes 2 and 3 is 0.001× $10^7$ units, or 10,000 units. Again, since the labels are independently detectable, the background contributed by the presence of one label will not usually interfere with the detection of the others.

At analyte concentrations of between 100 and 10,000 fmoles, probes 1 and 2 will have bound completely, with $10^5$ units of signal from probe 1 and $10^7$ units of signal from probe 2 detected. Probe 3 will bind up to $10^5$ fmoles (10 pmoles) of the analyte; since this probe is labeled at the same specific activity as the other probes, this will cause $10^9$ units of signal from probe 3 to be detected. The background contributed by label 3 will be $10^9 \times 0.001$, or $10^6$ units of label.

The foregoing explanation is illustrated in Table 2, below.

TABLE 2

| Amount of Target to be Detected (pmoles) | Probe 1 (units of signal) | Probe 2 (units of signal) | Probe 3 (units of signal) | Total Units of signal |
|---|---|---|---|---|
| 0.00001 | 1,000 | 1,000 | 1,000 | 1,000 units from Label 1<br>1,000 units from Label 2<br>1,000 units from Label 3 |
| 0.0001 | 10,000 | 10,000 | 10,000 | 10,000 units from Label 1<br>10,000 units from Label 2<br>10,000 units from Label 3 |
| 0.001 | 100,000 | 100,000 | 100,000 | 100,000 units from Label 1<br>100,000 units from Label 2<br>100,000 units from Label 3 |
| 0.01 | 100,000 | 1,000,000 | 1,000,000 | 100,000 units from Label 1<br>$10^6$ units from Label 2<br>$10^6$ units from Label 3 |
| 0.1 | 100,000 | 10,000,000 | 10,000,000 | 100,000 units from Label 1<br>$10^7$ units from Label 2<br>$10^7$ units from Label 3 |
| 1 | 100,000 | 10,000,000 | 100,000,000 | 100,000 units from Label 1<br>$10^7$ units from Label 2<br>$10^8$ units from Label 3 |
| 10 | 100,000 | 10,000,000 | 1,000,000,000 | 100,000 units from Label 1<br>$10^7$ units from Label 2<br>$10^9$ units from Label 3 |

As can be seen, unlike the situation illustrated in Example 1 in which the labels are indistinguishable and of different specific activities, in this embodiment the same linear relationship is maintained between the amount of analyte in the sample and the amount of signal detected. While the assay methodology of this mode of the invention is perfectly sound, it is possible that the detection device or method may not measure signals within one or more of the given ranges. As one example, if the methods of detecting each label do not accurately measure the 100,000 units of signal given off by Label 1, or the 10,000,000 units of signal for Label 2, or the 1,000,000,000 units of signal given off by Label 3, then the accuracy of the overall methodology is lessened. Obviously, however, the method or device used to detect one said label need not be the same device or method used to detect another said label.

However, if the detection methods are capable of accurately measuring signal generated from each label throughout its "effective detection range" (i.e., the range of analyte amounts which depend of the measurement of that particular label in the assay), and each label is nearly completely distinguishable from each other label, then this assay format has distinct advantages over the format illustrated in Example 1. Because the specific activities of the labels in this Example are the same, there is the same relationship between the amount of analyte and the amount of signal generated throughout the dynamic range of the assay. Therefore, this assay format permits detection of analyte with enhanced sensitivity as compared to the format of Example 1. As in Example 1, each probe must be targeted to a distinct region of the analyte, such that the probe does not compete for binding with the other probes.

EXAMPLE 3

Distinguishable Labels, Different Specific Activities

In a third and currently preferred embodiment, the invention is capable of detecting analyte across a broad range of potential analyte amounts or concentrations through the use of probes labeled with distinguishable labels which are present joined to each probe at a different specific activity.

As in Examples 1 and 2, to illustrate the present example it will be assumed that three labeled probes are targeted each to a different region of the analyte. As before, each probe is present in a different amount (1 fmole, 100 fmoles, and 10,000 fmoles for probes 1, 2 and 3, respectively) in order to detect a specific range of potential analyte which might be present in a sample.

As in Example 1, each probe is labeled at a different specific activity than is each other probe; thus, probe 1 is labeled at a specific activity of $10^8$ units of signal per pmole, probe 2 is labeled at $10^6$ units of signal per pmole, and probe 3 is labeled at $10^4$ units of signal per pmole. As a result, in this assay, the maximum amount of each probe is $10^5$ units per assay. Similarly to Example 2, each probe is separately distinguishable from each other probe. The present embodiment is illustrated in Table 3, below.

TABLE 3

| Amount of Target to be Detected (pmoles) | Probe 1 (units of signal) | Probe 2 (units of signal) | Probe 3 (units of signal) | Total Units of Signal | |
|---|---|---|---|---|---|
| 0.00001 | 1,000 | 10 | 0.1 | 1,000 | units from Label 1 |
| | | | | 10 | units from Label 2 |
| | | | | 0.1 | units from Label 3 |
| 0.0001 | 10,000 | 100 | 1 | 10,000 | units from Label 1 |
| | | | | 100 | units from Label 2 |
| | | | | 1 | units from Label 3 |
| 0.001 | 100,000 | 1,000 | 10 | 100,000 | units from Label 1 |
| | | | | 1,000 | units from Label 2 |
| | | | | 10 | units from Label 3 |
| 0.01 | 100,000 | 10,000 | 100 | 100,000 | units from Label 1 |
| | | | | 10,000 | units from Label 2 |
| | | | | 100 | units from Label 3 |
| 0.1 | 100,000 | 100,000 | 1,000 | 100,000 | units from Label 1 |
| | | | | 100,000 | units from Label 2 |
| | | | | 1,000 | units from Label 3 |
| 1 | 100,000 | 100,000 | 10,000 | 100,000 | units from Label 1 |
| | | | | 100,000 | units from Label 2 |
| | | | | 10,000 | units from Label 3 |
| 10 | 100,000 | 100,000 | 100,000 | 100,000 | units from Label 1 |
| | | | | 100,000 | units from Label 2 |
| | | | | 100,000 | units from Label 3 |

Because each label is separately distinguishable from each other label, each probe is detected without being overwhelmed by other probes. Because the specific activities of each labeled probe are different, the amount of signal obtained while detecting very small amounts of analyte is enhanced, while the amount of signal obtained while detecting very large amounts of analyte is attenuated. This feature is particularly advantageous when the detection method or device used to detect one or more of these labels is limited to a particular dynamic range. For example, in the presently illustrated situation, each of the three probes yields signal in the same range: 1,000 to 100,000 units of signal—thus, while the assay detects analyte over six (6) orders of magnitude, a detection device used to detect any one analyte only need be accurate over two orders of magnitude.

This latter fact has advantages in particular aspects of the present invention. For example, separately distinguishable labels may be detectable using a single instrument or detection method. In particularly preferred aspects of the invention disclosed below, separately detectable chemiluminescent labels are used. Specific chemiluminescent labels may be detected by measuring the emission of light in the same wavelength range over different periods of time, or over the same period of time using mathematical methods to resolve the signals, using a single luminometer. Additionally, the labels are present at different specific activities, which decreases the luminometer dynamic range necessary to detect analytes over a large concentration range. Therefore, whatever limitations may be inherent in the dynamic range of the luminometer do not limit the ability of the present invention to detect analyte over a greater concentration range, since separately detectable labels are used to cover this enhanced range, with each label being individually detectable within the intrinsic dynamic range of the instrument.

EXAMPLE 4

Application to Nucleic Acid Hybridization Assays

Although the invention is not limited to any particular format or label type, Applicant currently prefers to apply the invention to nucleic acid hybridization assays, using oligonucleotide probes and chemiluminescent acridinium ester labels.

The ability of various luminescent, fluorescent, and chemiluminescent labels to be separately detected from each other in a mixture has been described in, e.g., Woodhead et al., U.S. Pat. No. 5,656,207 and Nelson et al., U.S. Pat. No. 5,658,737, previously incorporated by reference herein. The latter reference, in particular, describes the use of different acridinium ester (AE) derivatives in a single assay and their ability to be separately detected in a number of formats. These formats include using chemiluminescent AE derivatives which emit light at different wavelengths, and separately detecting each label; using AE derivatives which react in a light emitting reaction at different rates and separately detecting the labels on the basis of reaction kinetics; and employing labels which react under different reaction conditions, such as pH, temperature, and the like.

Figure 1B:
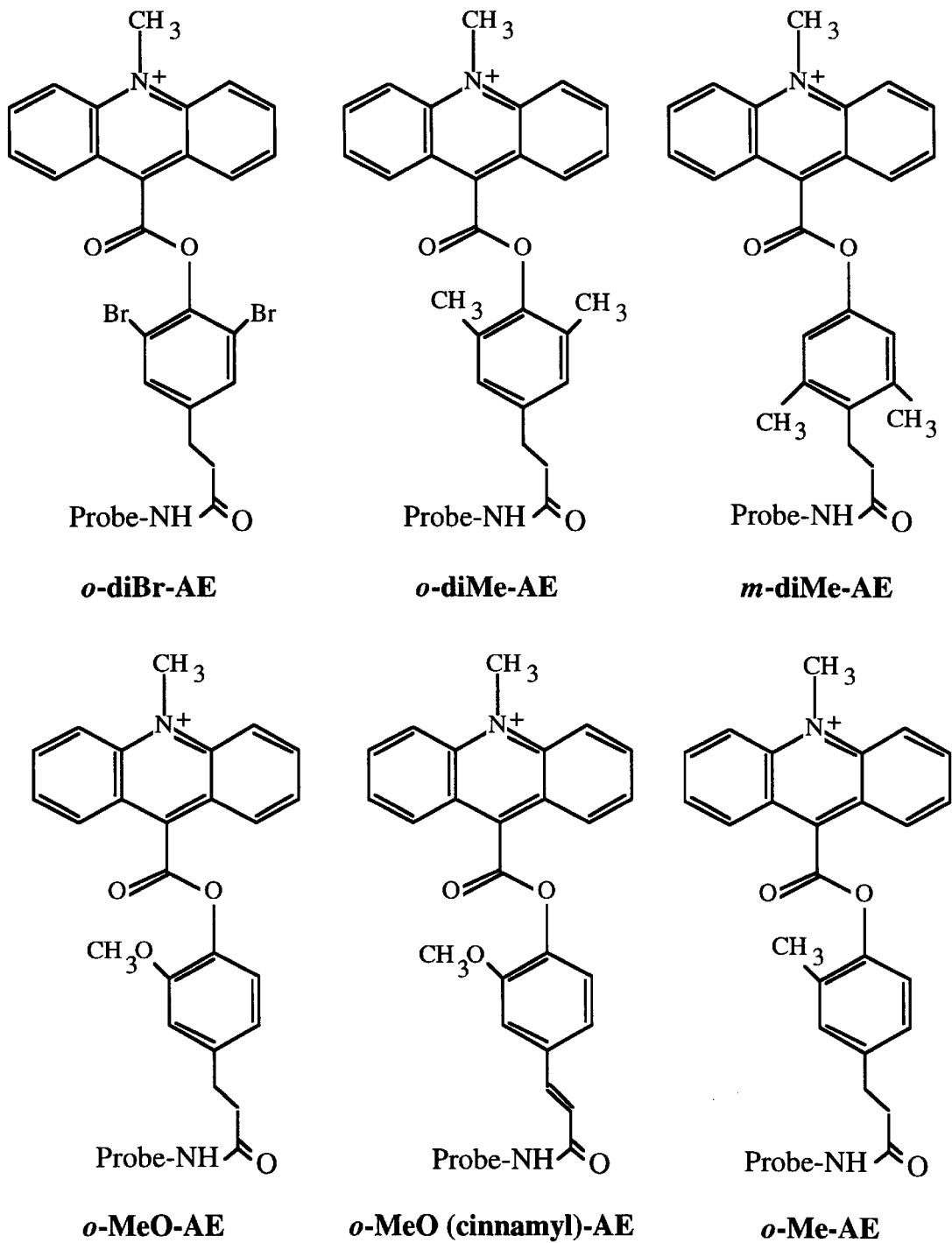
Figure 1C:
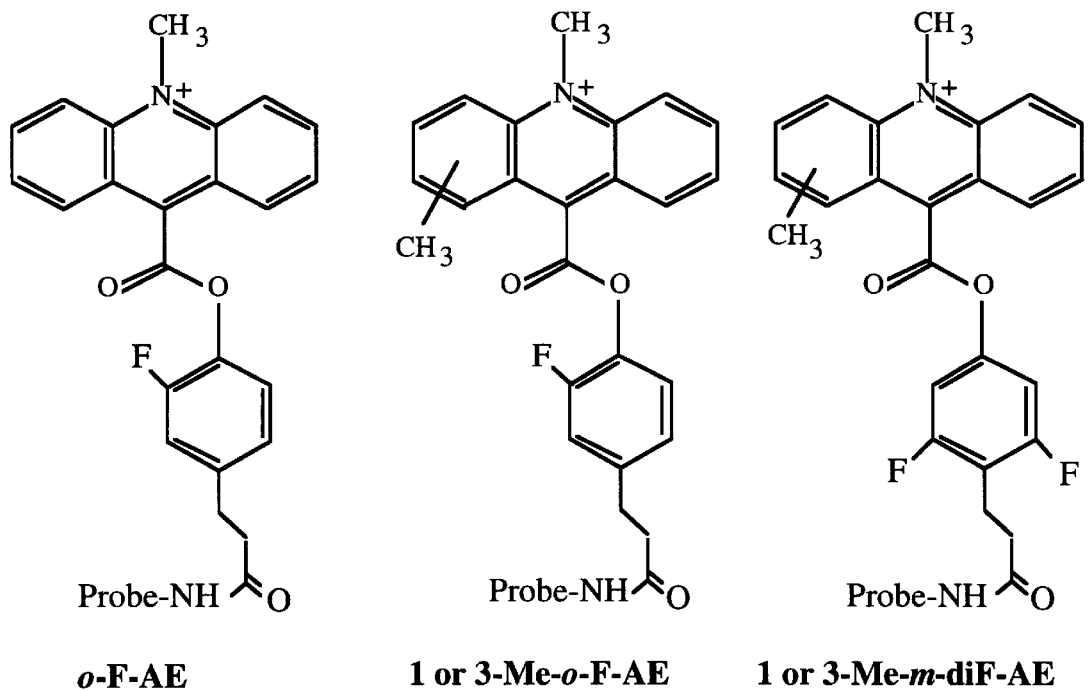

FIG. 1 shows the structure of several acridinium aryl ester compounds to which a linker moiety is attached; these acridinium ester compounds are indicated by a shorthand nomenclature as: standard-AE, naphthyl-AE, o-AE, 1 or 3-Me-AE, 2,7-diMe-AE, 4,5-diMe-AE, o-diBr-AE, o-diMe-AE, m-diMe-AE, o-MeO-AE, o-MeO(cinnamyl)-AE, o-Me-AE, o-F-AE, 1 or 3-Me-o-F-AE, and 1 or 3-Me-m-diF-AE. It will be understood that when these terms are used in the present application, they will refer to the corresponding acridinium aryl esters represented in this figure; 1-Me-AE, 1-Me-o-F-AE, and 1-Me-m-diF-AE are present in a mixture with their 3-methyl isomers; as used in this application, these nomenclatures will be understood to mean a mixture of the corresponding 1- and 3-methyl derivatives. o-MeO(cinnamyl)-AE is also referred to as o-MeO(c)-AE.

The skilled person will recognize that these terms refer to the chemiluminescent acridinium ester compounds themselves, and that the illustrated linkers to which they are attached are largely interchangeable with other linkers, such as linkers having a longer or shorter chain length, that are known in the art.

To illustrate the present invention, three of the above-mentioned labels were used: 1-Me-m-diF-AE, 1-Me-AE, and o-OMe(c)-AE. The signals emitted by these compounds are capable of being independently distinguished on the basis of their reaction kinetics. The 1-Me-m-diF-AE emits light extremely quickly after initiation of a chiluminescent reaction; the 1-Me-AE, has somewhat slower reaction kinetics, reaching a peak of light emission more slowly and emitting light over a longer time period than the 1-Me-m-diF-AE. The o-OMe(c)-AE has the slowest reaction kinetics of the three, and emits light over a longer period of time than either of the other compounds.

EXAMPLE 5

Illustration of Extension of Dynamic Range

In this example, the 1-Me-m-diF-AE, 1-Me-AE, and o-OMe(c)-AE derivatives were used in a homogeneous assay method as described in Arnold, et al., previously incorporated by reference herein. The 1-Me-m-diF-AE was used at a relatively high specific activity of $10^8$ rlu/pmole, which would be useful in the detection of analyte at the low end of the concentration range; the 1-Me-AE was used at a specific activity of $10^6$ rlu/pmole and the o-OMe(c)-AE was present at a specific activity of $10^4$ rlu/pmole. Other details of the labels and the assay protocol are shown below in Table 4.

TABLE 4

|  | 1-Me-m-diF-AE (Label 1) | 1-Me-AE (Label 2) | o-OMe(c)-AE (Label 3) |
|---|---|---|---|
| Specific Activity (rlu/pmole probe) | $10^8$ rlu/pmole | $10^6$ rlu/pmole | $10^4$ rlu/pmole |
| Label Input Amount (in rlu)* | $10^5$ rlu | $10^5$ in window ($3 \times 10^5$ rlu actually added) | $10^5$ in window ($4 \times 10^5$ rlu actually added) |
| Analyte Range | 0.01–1 fmole | 1–100 fmole | 0.1–10 pmole |
| Reading Window** | 0.0–0.6 seconds | 1.0–3.6 seconds | 4.0–10 seconds |
| Hydrolysis Rate ($t_{1/2}$) | 2.2 min. | 2.0 min. | 2.1 min. |

*The actual amount of rlu's added for the second and third labels was greater than $10^5$ rlu in order to assure that $10^5$ rlu of label was detected in each reading window; the amounts of each label were 0.001 pmoles for the first label, 0.3 pmoles for the second label, and 40 pmoles for the third label.
**The reaction kinetics were measured in 0.2 second intervals.

Figure 2:
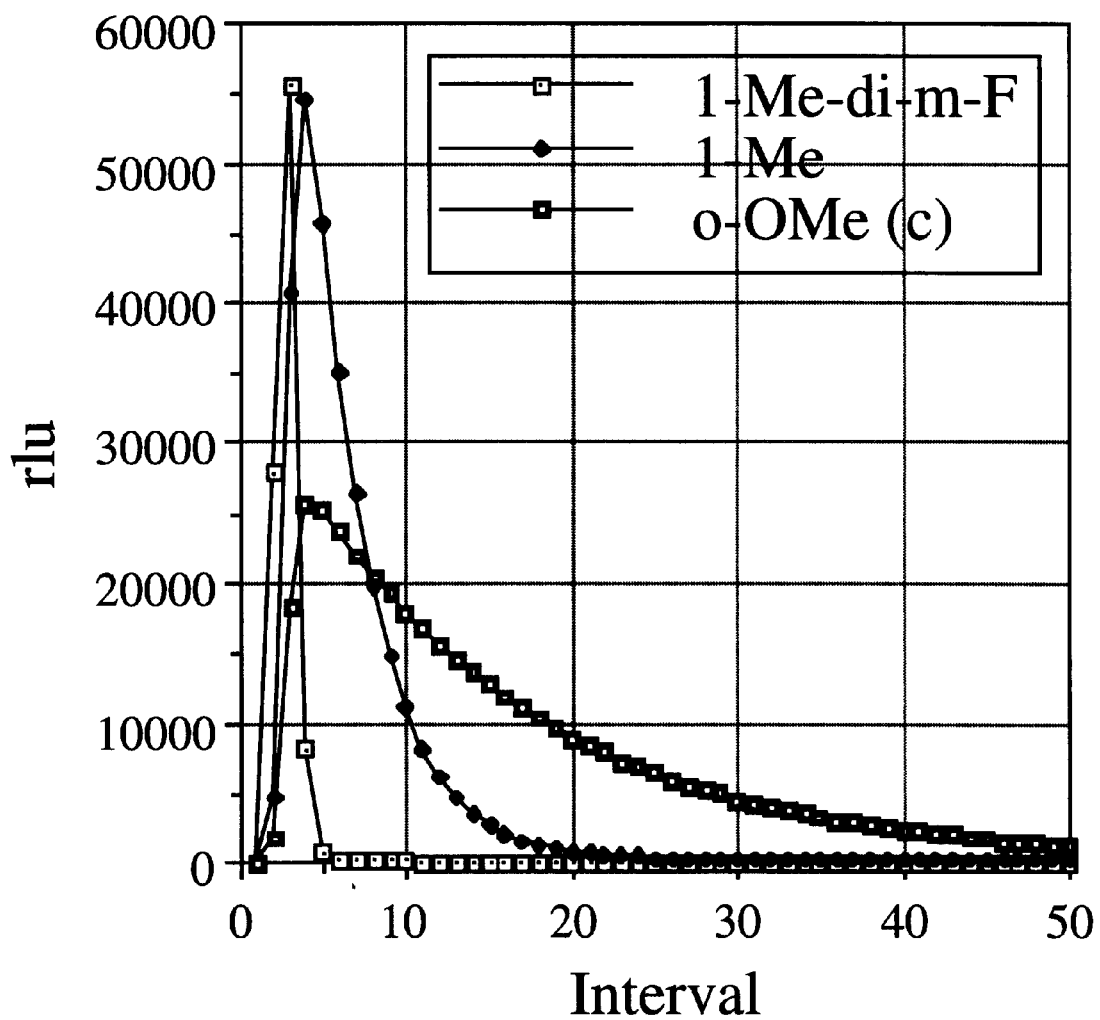
FIG. 2 is a plot wherein the y axis is the amount of light emitted by each of three labels, in relative light units (rlu), and the x axis is time. The three compounds are 1-Me-di-m-F-AE, 1-Me-AE and o-OMe(c)-AE. As shown by the plot, the kinetics of light emission for these three compounds permit their separate detection, with 1-Me-di-m-F-AE reacting most quickly, then 1-Me-AE, and o-OMe(c)-AE reacting over a longer period of time than the other compounds.

A plot of the light emission of each of these compounds, measured in relative light units (rlu), versus time is shown in FIG. 2. In this figure, the cheriluminescent reaction was initiated by simultaneously reacting all the labeling compounds with a triggering agent (in this case alkaline hydrogen peroxide). FIG. 2 shows that the majority of light emitted from the 1-Me-m-diF-AE is produced in the first half second of reaction. The 1-Me-AE emits light between 0 and 3 seconds, after which very little additional light is produced; during the period between 0.5 and 3 seconds very little interference is contributed by the 1-Me-m-diF-AE compound. The o-OMe(cinnamyl)-AE continues to emit light for at least 5 seconds after the 3 second point.

These labels may therefore be distinguished experimentally by measuring the light emitted during three well-defined time "windows", one window for each label. Additionally, because the time course of reaction for each compound is constant, it is possible to predict and subtract light emitted from the other labels in a window used for the measurement of a particular label's signal through a reiterative statistical calculation. Such a statistical calculation, as performed for two labels, is provided in Nelson et al., U.S. Pat. No. 5,658,737, previously incorporated by reference herein, at Example 3. It would be clearly within the capability of the skilled artisan to alter this calculation for the analysis and correction of signal obtained from three or more labels as well. Thus, a possible set of windows for the compounds above would be 0.0–0.6 seconds for the detection of 1-Me-m-diF-AE, 1.0–3.6 seconds for the detection of 1-Me-AE and 4.0–10 seconds for the detection of o-OMe (cinnamyl)-AE.

The hydrolysis rate mentioned in Table 4 is important only to the homogeneous assay method in which example was conducted, and is not crucial to the presently claimed methods or compositions.

Assuming that the labels are perfectly distinguishable, the theoretical profile of target amount versus the signal obtained from each label from its respective reading window is a follows:

TABLE 5

| Target (pmole) | Label 1 (rlu) | Label 2 (rlu) | Label 3 (rlu) |
|---|---|---|---|
| 0.00001 | 1000 | 10 | 0.1 |
| 0.00004 | 4000 | 40 | 0.4 |
| 0.00007 | 7000 | 70 | 0.7 |
| 0.0001 | $10^4$ | 100 | 1.0 |
| 0.0004 | $4 \times 10^4$ | 400 | 4.0 |
| 0.0007 | $7 \times 10^4$ | 700 | 7.0 |
| 0.001 | $10^5$ | 1000 | 10 |
| 0.004 | $10^5$ | 4000 | 40 |
| 0.007 | $10^5$ | 7000 | 70 |
| 0.01 | $10^5$ | $10^4$ | 100 |
| 0.04 | $10^5$ | $4 \times 10^4$ | 400 |
| 0.07 | $10^5$ | $7 \times 10^4$ | 700 |
| 0.10 | $10^5$ | $10^5$ | 1000 |
| 0.40 | $10^5$ | $10^5$ | 4000 |
| 0.70 | $10^5$ | $10^5$ | 7000 |
| 1.0 | $10^5$ | $10^5$ | $10^4$ |
| 4.0 | $10^5$ | $10^5$ | $4 \times 10^4$ |
| 7.0 | $10^5$ | $10^5$ | $7 \times 10^4$ |
| 10.0 | $10^5$ | $10^5$ | $10^5$ |

To verify this hypothetical analysis, each of these three acridinium ester labels was mixed in the proportions indicated above in a solution containing 30 µl of 10 mM lithium succinate (pH 5.0) and 0.1% (w/v) lithium lauryl sulfate, 100 μl of 100 mM lithium succinate (pH 5.0), 8.5% (w/v) lithium lauryl sulfate, 1.5 mM EDTA, 1.5 mM EGTA, and 300 μl of 600 mM sodium borate (pH 8.5), 1% (v/v) TRITON® X-100 (octylphenoxy polyethoxyethanol). This solution was placed into a LEADER® 50 luminometer, and detected with an injection of 200 μl 0.1% (v/v) $H_2O_2$ in 1 mM $HNO_3$, followed by an injection of 200 μl of 1.5 N NaOH. Light emission was measured at 0.2 second intervals after initiation of the chemiluminescent reaction. The "reading windows" were the same as shown in Table 4. The results are shown in below in Table 6.

TABLE 6

| Target (pmole) | Label 1 | Label 2 | Label 3 |
|---|---|---|---|
| 0.00001 | 1080 | 54 | 63 |
| 0.00004 | 4601 | 188 | 86 |
| 0.00007 | 7697 | 311 | 198 |
| 0.0001 | 10197 | 380 | 234 |
| 0.0004 | 40959 | 1308 | 704 |
| 0.0007 | 66174 | 2295 | 1166 |
| 0.001 | 90979 | 3117 | 1810 |
| 0.004 | 93129 | 8353 | 2156 |
| 0.007 | 97467 | 12604 | 2360 |
| 0.01 | 97010 | 16285 | 2516 |
| 0.04 | 144034 | 61496 | 5653 |
| 0.07 | 184345 | 102891 | 8022 |
| 0.10 | 179248 | 142326 | 10524 |
| 0.40 | 180289 | 146349 | 14517 |
| 0.70 | 180901 | 153413 | 19049 |
| 1.0 | 177833 | 154494 | 21023 |
| 4.0 | 197599 | 232885 | 59264 |
| 7.0 | 202855 | 292157 | 90589 |
| 10.0 | 220880 | 346219 | 121487 |

As this table shows, the results obtained by mixing these labels and detecting each one in a separate detection "window" are very similar to those predicted in Table 5 above. As Table 5 predicts, Label 1 gives a linear response until it reaches saturation, at a level of $10^5$ rlu. Similarly, Label 2 permits detection to a theoretical target amount of 0.1 pmoles, with the signal given off by Label 2 also plateauing at a level of $10^5$ rlu. Lastly, the signal emitted from Label 3 rises above background at a theoretical target level of between 0.01 and 0.04 pmoles and increases proportionally to the amount of target to the maximum theoretical target amount of 10 pmoles. In comparison, the data actually obtained and reported in Table 6 correspond well with the theoretical values of Table 5.

The experiments in this example were conducted in the absence of target and without each label being joined to a oligonucleotide probe. However, those of skill in the art will recognize that the present results are predicted to be similar to those obtained when each label is joined to a probe at the indicated specific activity in an actual assay of target analyte across the ranges from 0.01 fmoles to 10 pmoles, so long as the probes are each targeted to a different region of the target analyte.

EXAMPLE 6

Extending the Dynamic Range of More Than One Analyte

The present invention may be used in conjunction with four or more separately detectable labels to extend the dynamic range for the detection of two or more analytes in a multiple analyte assay system. Such labels may be of any type, including without limitation: radioactive, fluorescent, chemiluminescent, chromogeneic, and enzyme- or substrate-linked labels. Examples of multiple analyte assay systems are described in e.g., Woodhead et al., U.S. Pat. No. 5,656,207 and Nelson et al., U.S. Pat. No. 5,658,737, both of which were previously incorporated by reference herein; these references describe particular multiple analyte assay systems; however, as the previous discussion makes clear, the invention can predictably be used in any assay system. Therefore, the invention should not be construed as being limited to the systems exemplified above.

In this format, at least two labels are used to detect each different analyte, with the dynamic range of the assay for the detection of each analyte extended through the use of at least two labeled probes targeted to different regions of each said analyte. As in the previous example, each analyte is detected using at least two such probes labeled with distinguishable labels; preferably probes targeted to the same analyte are labeled at different specific activities, with the amount of each probe corresponding to the upper limit of the range of analyte amounts which that probe is intended to detect.

Thus, the result of the assay format of this example is that the separate detection or quantification of two or more analytes is permitted, with the consequence that each analyte is accurately measured over a wider range of potential concentrations than would otherwise be possible.

EXAMPLE 7

Demonstration of Extended Dynamic Range Using Oligonucleotide Probes

To demonstrate the ability of one embodiment of the present invention to specifically detect analyte across a broad range of analyte amount or concentration, the following experiment was done.

A synthetic RNA molecule 48 bases in length was used as the target molecule. Two different oligonucleotide probes complementary to non-overlapping, unique areas of the target RNA molecule (Probe 1 (comprising 22 nucleotides) and Probe 2 (comprising 18 nucleotides)) were labeled with different chemiluminescent labels; Probe 1 was labeled with an N-acridinium phenyl ester having a fluorine substitution at the ortho position of the phenyl ring (termed o-F-AE), and Probe 2 was labeled with an N-acridinium phenyl ester which has a methyl group at the 2' position of the acridinium ring (termed 2-Me-AE). Unsubstituted acridinium ester containing a NHS linker at the 4 position of the phenyl moiety has the nomenclature (4-(2-succinimidyloxycarbonyl ethyl) phenyl-10-methylacridinium 9-carboxylate fluorosulfonate).

A chemiluminescent reaction employing the o-F-AE label has sufficiently fast reaction kinetics as compared to that of the 2-Me-AE label that the signals obtained from the two compounds upon a single initiation event can be distinguished from each other by monitoring the resulting light emission over a given time period at regular intervals. The respective signals obtained from the two labels can be even more precisely quantified by employing a simple reiterative mathematical technique. These methods and representative labels able to be used in this format are disclosed in greater detail in Woodhead et al., U.S. Pat. No. 5,656,207 and Nelson et al., U.S. Pat. No. 5,658,737; both of these references are incorporated by reference herein in their entirety.

The oligonucleotides were linked to the acridinium ester (AE) labels through the use of a linker arm, as shown in FIG. 1, attached to the phenyl ring. The linker was then joined to the oligonucleotide via a non-nucleotide linker, which was incorporated into the oligonucleotide chain. See, e.g., Arnold, et al., U.S. Pat. No. 5,656,744, which enjoys common ownership with the present invention, and is now incorporated by reference herein. In this method the linker arm moiety to which the label will be attached is placed at a predetermined position within the oligonucleotide during synthesis. The solid-phase synthesis of oligonucleotides is well known in the art and is described in Brown & Brown, *Modern Machine-Aided Methods of Oligodeoxyribonucleotide Synthesis* in *Oligonucleotides and Analogues-A Practiced Approach* (1991).

Acridinium ester derivatives may be joined to the linker arm of the hybridization probe using techniques well known in the art. Preferably, Applicants use the methods described in Nelson et al., *Detection of Acridinium Esters by Chemiluminescence* in *Non-Isotopic Probe Techniques* (Academic Press 1992), incorporated by reference herein, and Arnold et al., supra, previously incorporated by reference herein.

In one such method, an N-hydroxysuccinimide (NHS) ester of acridinium (e.g., 4-(2-succinimidyloxycarbonyl ethyl) phenyl-10-methylacridinium 9-carboxylate fluorosulfonate) is synthesized generally as described in Weeks et al., *Clin. Chem.* 29: 1474–1478 (1983), incorporated by reference herein, and Nelson et al., U.S. Pat. No. 5,658,737, previously incorporated by reference herein. Reaction of the primary amine of the linker arm:hybridization probe conjugate with the selected NHS-acridinium ester is performed as follows. The oligonucleotide hybridization probe:linker arm conjugate synthesized as described above is vacuum-dried in a Savant SPEED-VAC™ drying apparatus, then dissolved in 8 µl of 0.125 M HEPES buffer (pH 8.0) in 50% (v/v) DMSO. To this solution is added 2 µl of 25 mM of the desired NHS-acridinium ester. The solution is mixed and incubated at 37° C. for 20 minutes.

An additional 3 µl of 25 mM NHS-acridinium ester in DMSO is added to the solution and mixed gently, then 2 µl of 0.1 M HEPES buffer (pH 8.0) is added, mixed, and the tube is allowed to incubate for an additional 20 minutes at 37° C. The reaction is quenched with the addition of 5 µl 0.125 M lysine in 0.1 M HEPES buffer (pH 8.0) in DMSO, which is mixed gently into the solution.

The labeled oligonucleotide is recovered from solution by the addition of 30 µl 3 M sodium acetate buffer (pH 5.0), 245 µl water, and 5 µl of 40 mg/ml glycogen. Six hundred forty microliters of chilled 100% ethanol is added to the tube, and the tube is held on dry ice for 5 to 10 minutes. The precipitated labeled nucleic acids are sedimented in a refrigerated microcentrifuge at 15,000 rpm using a standard rotor head. The supernatant is aspirated off, and the pellet is redissolved in 20 µl 0.1 M sodium acetate (pH 5.0) containing 0.1% (w/v) sodium dodecyl sulfate (SDS).

In this case, both Probe 1 and Probe 2 contained modified sugar moieties wherein the 2' position of the ring was substituted with a methoxy group rather than —H (deoxyribose) or —OH (ribose). The use of modified oligonucleotides is not critical (or even important) to the present invention, which can be used with unmodified oligonucleotides as well.

The first experiments were conducted as follows: Probe 1 was conjugated essentially as described above with o-F-AE at a specific activity of approximately $7 \times 10^7$ rlu/pmole. Probe 2 was conjugated with the 2-Me-AE label at a specific activity of approximately $1 \times 10^8$ rlu/pmole, and mixed with unlabeled probe as described below to yield a lower specific activity detected as a difference of approximately 100-fold between the detectable signals of Probe 1 and Probe 2.

To test the two separate probe:label combinations in an actual assay, 11 fmoles of labeled Probe 1 were hybridized to various amounts (0.00, 0.01, 0.02, 0.05, 0.20, 0.50, 2, 5, 20, 50, 200, 500, 2000, and 5000 fmoles) of the target RNA. At the same time, 5 fmoles labeled Probe 2 plus 15 pmoles unlabeled Probe 2 were also hybridized in separate reaction mixtures to the same amounts of target. Each set consisted of 100 µl hybridization reactions containing 100 mM lithium succinate (pH 5.0), 8.5% (w/v) lithium lauryl sulfate, 1.5 mM EDTA, and 1.5 mM EGTA and each reaction mixture was incubated at 50° C. for 50 minutes. Three hundred microliters of a solution containing 150 mM $Na_2B_4O_7$ (pH 8.6) and 1% (v/v) TRITON® X-100 were added to each reaction, and the mixtures incubated at 50° C. for 11 minutes. The reaction mixtures were then placed into a LEADER® 50 luminometer, and a chemiluminescent reaction initiated in each mixture upon the injection of 200 µl 0.1% (v/v) $H_2O_2$ and 1 mM $HNO_3$, followed by 200 µl of 1.5 N NaOH. Chemiluminescence was read at a wavelength range from 300 to 650 nm for 2 seconds following the second injection.

The results are shown in Table 7 below and graphically illustrated in FIGS. 3A and 3B.

TABLE 7

Analyte Assayed and Detected in Individual Reaction Mixtures

| fmoles Target RNA | rlu output [Probe 1 (o-F-AE)] | rlu output [Probe 2 (2-Me-AE)] |
|---|---|---|
| 0.00 | 53 | 0 |
| 0.01 | 428 | 0 |
| 0.02 | 912 | 0 |
| 0.05 | 2209 | 0 |
| 0.2 | 9181 | 0 |
| 0.5 | 22968 | 0 |
| 2.0 | 82545 | 0 |
| 5.0 | 177543 | 903 |
| 20.0 | 264501 | 1673 |
| 50.0 | 311928 | 3979 |
| 200.0 | 324618 | 15304 |
| 500.0 | 322676 | 39502 |
| 2000.0 | 351596 | 158033 |
| 5000.0 | 330214 | 275699 |

Figure 3A:
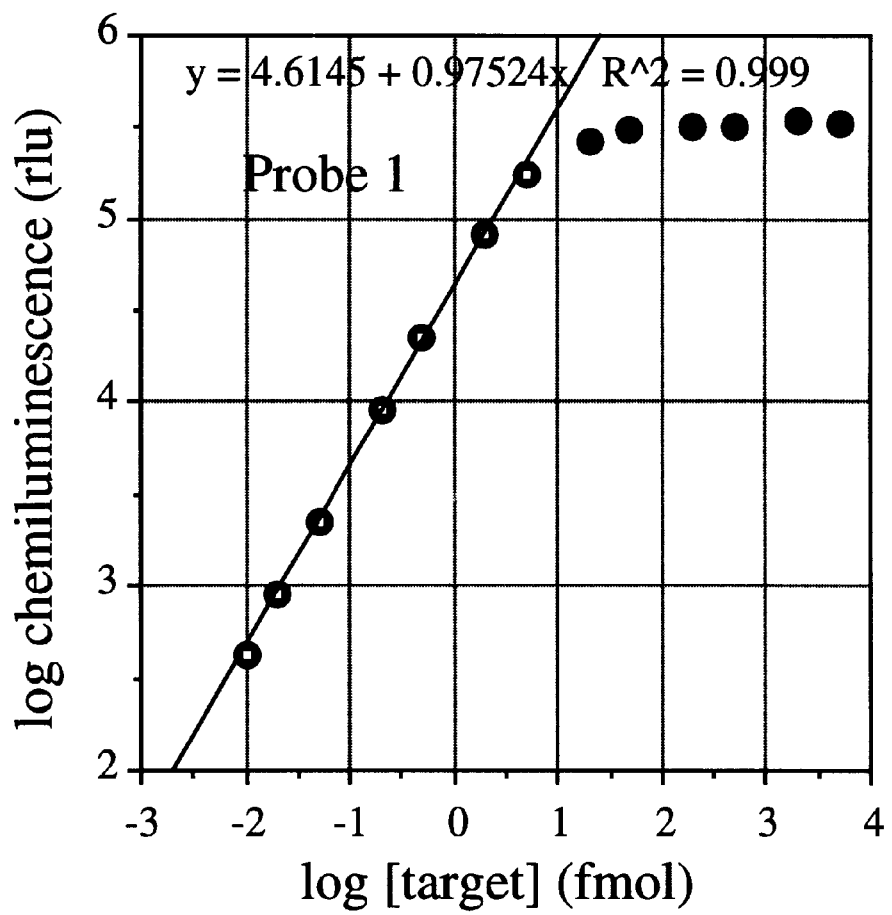
FIGS. 3A and 3B are plots of signal obtained from two different, and differently labeled, oligonucleotide probes directed to the same target RNA analyte in separate experiments.
Figure 3B:
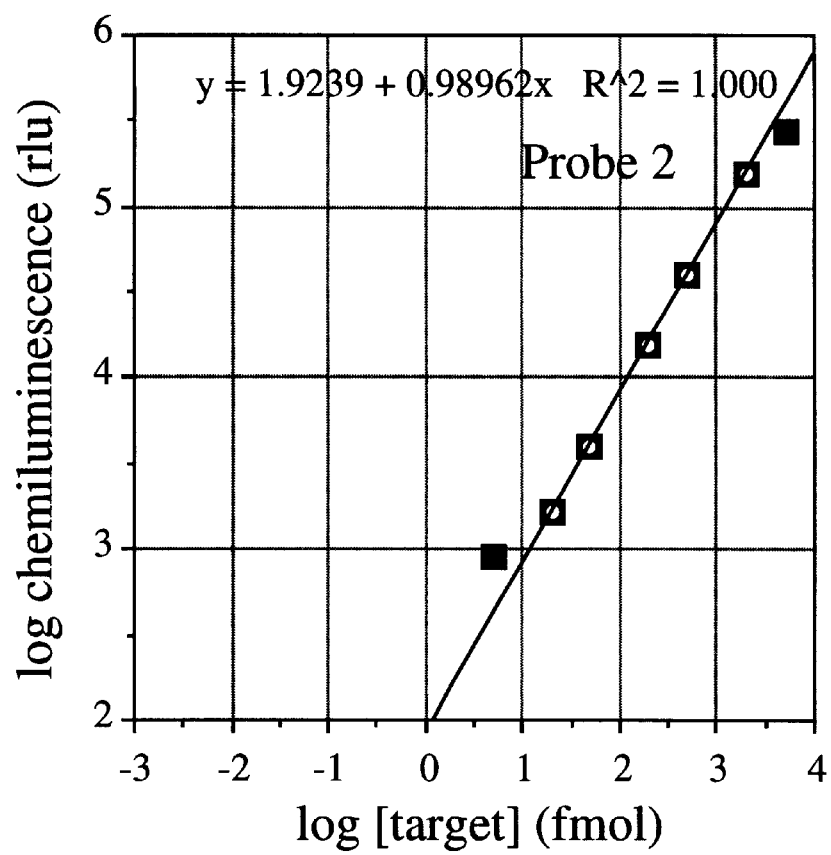

As can be seen in Table 7 and FIGS. 3A and 3B, when assayed in separate reactions, the o-F-AE label associated with Probe 1 emitted an increasing amount of light with increasing amount of analyte. The response was a linear one from about 0.01 fmoles to about 5 fmoles of the RNA target. Increasing the amount of analyte beyond about 5 fmoles led to a "plateau" effect.

By contrast, the 2-Me-AE associated with Probe 2 was detected at a 100-fold lower amount of detectable signal than that of the o-F-AE label of Probe 1. Thus the amount of light emitted by target-bound Probe 2 only became detectable in this experiment at higher analyte amounts, and a linear response (again, when plotted as a function of the log of the analyte concentration) is seen within a range of analyte amounts of from about 20 fmoles to about 2000–5000 fmoles of the target RNA.

These experiments resulted in the generation of standard curves for each of the two labels, present at different specific activities. It is not necessary when generating such independent standard curves to utilize two probes directed to different, substantially non-overlapping regions of the target analyte. In fact, a single probe utilizing a single label at different specific activities could be used to provide similar standard curves.

However, such probes would not be capable of functioning to substantially extend the dynamic range of accurately detectable analyte concentrations of the assay in a "single vessel" or simultaneous assay, as do the reagents of the methods claimed herein. As stated above, the addition of a single probe labeled with the same label at two different specific activities into an assay vessel would result in the probe being present at a third "average" specific activity, which could possibly change the range of concentrations detectable as compared to each individual different probe mixture, but it would not extend the dynamic range of the assay beyond the 2.5 to 3 logs characteristic of each label, as illustrated in FIGS. 3A and 3B.

To demonstrate a single-vessel assay according to the present invention, both labeled Probe 1 and labeled Probe 2 were combined in single hybridization mixtures with varying amounts of analyte. As in the previous experiment of this Example, Probe 2 was detected at 100-fold lower amount of detectable signal than Probe 1. Eleven fmoles o-F-AE labeled Probe 1 and 5 fmoles 2-Me-AE labeled Probe 2 was combined with 15 pmoles unlabeled Probe 2 in a hybridization buffer containing 100 mM lithium succinate (pH 5.0), 8.5% (w/v) lithium lauryl sulfate, 1.5 mM EDTA, and 1.5 mM EGTA and various concentrations of RNA target, as before. Each reaction mixture was incubated at 50° C. for 50 minutes.

Three hundred microliters of a solution containing 150 mM $Na_2B_4O_7$ (pH 8.6) and 1% (v/v) TRITON® X-100 were added to each reaction, and the mixtures incubated at 50° C. for 11 minutes. The reaction mixtures were then placed into a LEADER® 50 luminometer, and a chemiluminescent reaction initiated in each mixture upon the injection of 200 $\mu l$ 0.1% (v/v) $H_2O_2$ and 1 mM $HNO_3$, followed by 200 $\mu l$ of 1.5 N NaOH. Chemiluminescence was read for 2 seconds following the second injection, with light collected over 40 millisecond intervals during this period. The signal emitted by each label was resolved as follows. The resulting raw data were then subjected to a reiterative mathematical calculation using the sum of the light emitted during two interval ranges within the time period, referred to by the number of the 40 millisecond intervals following initiation of the chemiluminescent reaction; for this example these were: intervals 1–5 and intervals 30–50.

Samples containing only one labeled probe were used as standards for data analysis. For each standard the ratio between the sum of the rlu values obtained in the first time interval and the sum of the RLU values obtained in the second time interval was determined (Σ RLU 30–50/Σ RLU 1–5). The chemiluminescent signals measured in intervals 30–50 (in RLU) were added together and then divided by the ratio obtained for the 2-Me-AE standard. The resulting figure is the amount of RLU contributed in intervals 1–5 by 2-Me-AE-labeled probe. This amount, subtracted from the total RLU in intervals 1–5, gives the amount of RLU contributed in these intervals by o-F-AE. The latter number, when multiplied by the standard ratio for the two time periods obtained for o-F-AE), yields the RLU within the intervals 30–50 which were contributed by o-F-AE-labeled probe. When this figure is subtracted from the total RLU in intervals 30–50, a corrected value for the RLU contributed by 2-Me-AE in this interval is yielded. This number was used to repeat the calculation described above until the RLU contribution by o-F-AE in intervals 30–50 did not change within the chosen number of significant figures. These corrected data are reported below.

TABLE 8

Analyte Assayed and Detected in Single Reaction Mixtures

| fmoles Target RNA | rlu output [Probe 1 (o-F-AE)] | rlu output [Probe 2 (2-Me-AE)] |
|---|---|---|
| 0.00 | 59 | 63 |
| 0.01 | 573 | 31 |
| 0.02 | 1233 | 31 |
| 0.05 | 2893 | 0 |
| 0.2 | 11068 | 0 |
| 0.5 | 27139 | 31 |
| 2.0 | 93535 | 189 |
| 5.0 | 204984 | 600 |
| 20.0 | 271543 | 2277 |
| 50.0 | 315697 | 4428 |
| 200.0 | 314792 | 15974 |
| 500.0 | 301076 | 39036 |
| 2000.0 | 321450 | 153234 |
| 5000.0 | 328863 | 279105 |

Figure 4:
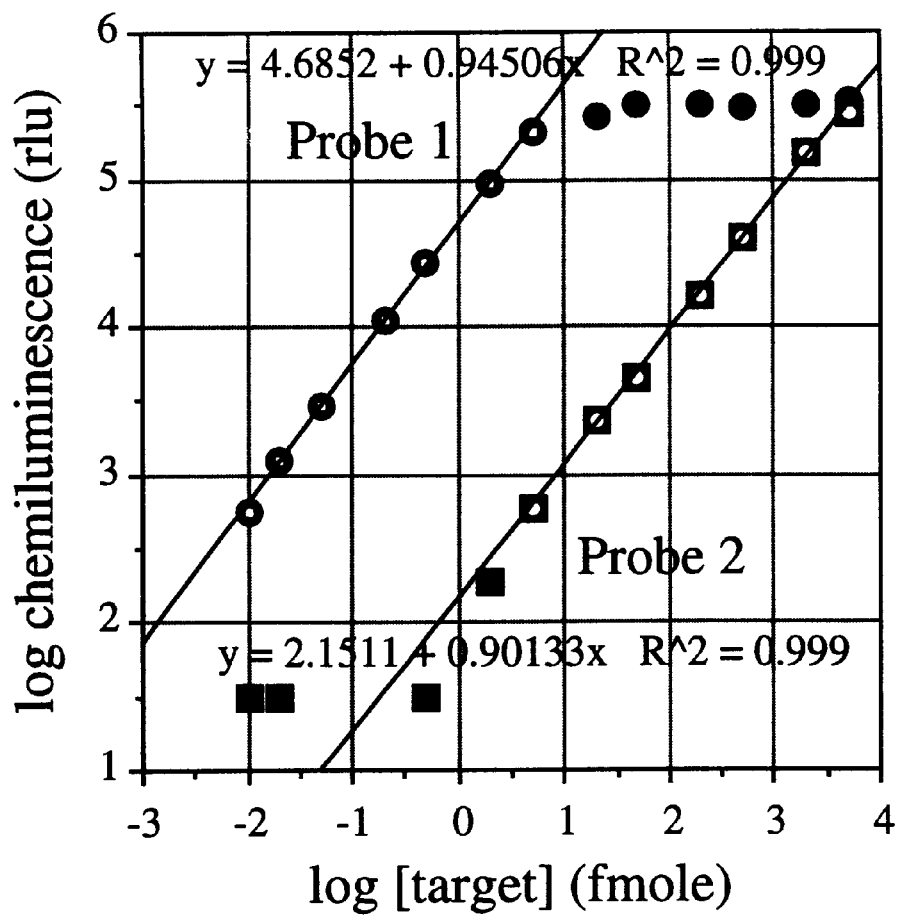
FIG. 4 is a plot of signal obtained from two different, and differently labeled, oligonucleotide probes directed to the same target RNA analyte. Chemiluminescence was initiated and detected simultaneously for both labels in the same reaction mixture. Probes, labels and analyte were the same as in FIGS. 3A and 3B.

These data demonstrate the ability of the methods of the present invention to extend the dynamic range for detection of a given analyte. As can be seen in FIG. 4, the results of this experiment closely resembles a composite of FIGS. 3A and 3B. However, the method of the present invention, which requires the probes to be directed to different target regions of the same analyte, in this case permits the detection and/or quantification of the analyte over 6 logs of possible target concentrations in a single tube assay. This assay format could therefore be used to detect or measure an analyte sample within this extended range of concentrations without prior knowledge of the analyte concentration in the sample to be tested.

Additionally, FIG. 4 demonstrates that the use of independently detectable labels at different specific activities in the methods of the present invention permits the detection of at least 6 logs of analyte concentrations to remain within the luminometer reporting range. Even further expansion of the dynamic range of the assay is possible, for example through the addition of a greater number of probes linked to independently detectable labels would permit even further expansion of the dynamic range of the assay; still, the luminometer reporting range would remain the same. In this way, an assay can be custom designed to the most accurate reporting range of the instrument or method to be used for detection.

The preceding examples are intended to illustrate rather than limit the present invention, which is defined solely by the claims which conclude this specification.

What is claimed is:

1. A method for detecting an analyte in a sample comprising the steps of:
   providing a labeled probe reagent comprising two or more labeled probes, each of the labeled probes comprising a different, separately detectable label joined to a probe that specifically binds to a target region of an analyte, wherein each probe specifically binds to a target region that differs from that bound by another probe in the labeled probe reagent;
   contacting
   i) a sample containing the analyte, and
   ii) the labeled probe reagent, wherein each of the labeled probes is present in a predetermined molar amount sufficient to specifically bind to a predetermined amount of the analyte, and wherein the predetermined molar amount of each labeled probe differs from that of another labeled probe present in the labeled probe reagent thereby allowing the labeled probe reagent to detect the analyte over a concentration range that is greater than the concentration range of the analyte detected by one labeled probe present in the labeled probe reagent;

incubating the sample and the labeled probe reagent under conditions favoring specific binding of the probes with the analyte, thereby forming at least one specific binding complex comprising at least one labeled probe and the analyte; and detecting at least one separately detectable label present in a specific binding complex, thereby indicating that the analyte is present in the sample in a concentration range detected by the separately detectable label detected, wherein each separately detectable label is distinguishable from another separately detectable label.

2. The method of claim 1, wherein the incubating and detecting steps are performed in a single vessel.

3. The method of claim 1, wherein the contacting, incubating and detecting steps are performed in a single vessel.

4. The method of claim 1, wherein the labeled probe reagent of the providing step comprises labeled probes in which each different, separately detectable label is a luminescent compound.

5. The method of claim 4, wherein each different, separately detectable label is a fluorescent compound or a chemiluminescent compound.

6. The method of claim 4, wherein the labeled probe reagent comprises at least one labeled probe comprising a separately detectable label that is a fluorescent compound and at least one labeled probe comprising a separately detectable label that is a chemiluminescent compound.

7. The method of claim 4, wherein the labeled probe reagent comprises at least one labeled probe comprising a separately detectable label that is a first chemiluminescent compound and at least one labeled probe comprising a separately detectable label that is a second chemiluminescent compound.

8. The method of claim 7, wherein the first chemiluminescent compound is selected from the group consisting of standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE and 1- or 3-methyl-meta-difluoro-AE; and wherein the second chemiluminescent compound is selected from the group consisting of standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE and 1- or 3-methyl-meta-difluoro-AE, provided that the first chemiluminescent compound is different from the second chemiluminescent compound.

9. The method of claim 8, wherein the first chemiluminescent compound is ortho-fluoro-AE, and wherein the second chemiluminescent compound is 2-methyl-AE.

10. The method of claim 7, wherein the labeled probe reagent further comprises at least one labeled probe comprising a separately detectable label that is a third chemiluminescent compound.

11. The method of claim 10, wherein the first chemiluminescent compound is selected from the group consisting of standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE and 1- or 3-methyl-meta-difluoro-AE;

wherein the second chemiluminescent compound is selected from the group consisting of standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE and 1- or 3-methyl-meta-difluoro-AE; and wherein the third chemiluminescent compound is selected from the group consisting of standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE and 1- or 3-methyl-meta-difluoro-AE, provided that the first, second and third chemiluminescent compounds differ from each other.

12. The method of claim 11, wherein the first chemiluminescent compound is 1- or 3-methyl-meta-difluoro-AE, wherein the second chemiluminescent compound is 1- or 3-methyl-AE, and wherein the third chemiluminescent compound is ortho-methoxy(cinnamyl)-AE.

13. The method of claim 1, wherein the analyte is a protein, nucleic acid, carbohydrate or lipid.

14. The method of claim 1, wherein the analyte is a nucleic acid.

15. The method of claim 1, wherein each of the labeled probes is a labeled protein or a labeled nucleic acid.

16. The method of claim 15, wherein each of the labeled probes is a labeled nucleic acid.

17. The method of claim 16, wherein each of the labeled probes is a labeled oligonucleotide.

18. The method of claim 1, wherein each of the labeled probes has a different specific activity, such that a probe having a relatively high specific activity is present in a molar amount that is lower than a molar amount of a probe having a relatively low specific activity.

19. The method of claim 1 or claim 18, wherein the providing step provides a labeled probe reagent in which each of the labeled probes is present in a molar amount that differs by at least 10-fold from that of each other labeled probe.

20. The method of claim 1 or claim 18, wherein the providing step provides a labeled probe reagent in which each of the labeled probes is present in a molar amount that differs by at least 100-fold from that of each other labeled probe.

21. The method of claim 1 or claim 18, wherein the providing step provides a labeled probe reagent in which each of the labeled probes is present in a molar amount that differs by at least 1,000-fold from that of each other labeled probe.

22. The method of claim 1 or claim 18, wherein the providing step provides a labeled probe reagent in which each of the labeled probes is present in a molar amount that differs by at least 10,000-fold from that of each other labeled probe.

23. The method of claim 18, wherein the labeled probe reagent comprises labeled probes in which each different, separately detectable label is a luminescent compound.

24. The method of claim 23, wherein each different, separately detectable label is a fluorescent compound or a chemiluminescent compound.

25. The method of claim 23, wherein the labeled probe reagent comprises at least one labeled probe comprising a separately detectable label that is a fluorescent compound and at least one labeled probe comprising a separately detectable label that is a chemiluminescent compound.

26. The method of claim 23, wherein the labeled probe reagent comprises at least one labeled probe comprising a separately detectable label that is a first chemiluminescent compound and at least one labeled probe comprising a separately detectable label that is a second chemiluminescent compound.

27. The method of claim 26, wherein the first chemiluminescent compound is selected from the group consisting of standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE and 1- or 3-methyl-meta-difluoro-AE; and wherein the second chemiluminescent compound is selected from the group consisting of standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE and 1- or 3-methyl-meta-difluoro-AE, provided that the first chemiluminescent compound is different from the second chemiluminescent compound.

28. The method of claim 27, wherein the first chemiluminescent compound is ortho-fluoro-AE, and wherein the second chemiluminescent compound is 2-methyl-AE.

29. The method of claim 28, wherein the labeled probe reagent further comprises at least one labeled probe comprising a separately detectable label that is a third chemiluminescent compound.

30. The method of claim 29, wherein the first chemiluminescent compound is selected from the group consisting of standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE and 1- or 3-methyl-meta-difluoro-AE;

wherein the second chemiluminescent compound is selected from the group consisting of standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE and 1- or 3-methyl-meta-difluoro-AE; and wherein the third chemiluminescent compound is selected from the group consisting of standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE and 1- or 3-methyl-meta-difluoro-AE, provided that the first, second and third chemiluminescent compounds differ from each other.

31. The method of claim 30, wherein the first chemiluminescent compound is 1- or 3-methyl-meta-difluoro-AE, wherein the second chemiluminescent compound is 1- or 3-methyl-AE, and wherein the third chemiluminescent compound is ortho-methoxy(cinnamyl)-AE.

32. A method for detecting an analyte in a sample comprising the steps of:

providing a probe reagent comprising at least two labeled probes, each of the labeled probes comprising
a different target-binding nucleic acid that binds specifically to the analyte, and
a label that is separately detectable and distinguishable from a label on another labeled probe in the probe reagent, wherein each of the labeled probes is present in a predetermined amount sufficient to specifically bind to a predetermined amount of the analyte, and wherein the predetermined amount of each labeled probe differs from that of another labeled probe in the probe reagent such that the probe reagent can detect the analyte over a concentration range greater than the concentration range of the analyte detected by a single labeled probe present in the probe reagent;

contacting a sample containing the analyte and the probe reagent;

incubating the sample and the probe reagent under conditions favoring specific binding of the analyte and the target-binding nucleic acid, thereby forming a binding complex comprising the analyte and at least one labeled probe; and measuring a luminescent signal resulting from at least one separately detectable label present in the binding complex, thereby indicating presence of the analyte in the sample.

33. The method of claim 32, wherein the providing step provides a probe reagent in which each of the labeled probes is present in a molar amount that differs by at least 10-fold from that of each other labeled probe.

34. The method of claim 32, wherein the providing step provides a probe reagent in which each of the labeled probes is present in a molar amount that differs by at least 100-fold from that of each other labeled probe.

35. The method of claim 32, wherein the providing step provides a probe reagent in which each of the labeled probes is present in a molar amount that differs by at least 1,000-fold from that of each other labeled probe.

36. The method of claim 32, wherein the providing step provides a probe reagent in which each of the labeled probes is present in a molar amount that differs by at least 10,000-fold from that of each other labeled probe.

37. The method of claim 32, 33, 34, 35 or 36, wherein each of the labeled probes has a different specific activity, such that a probe having a relatively high specific activity is present in a lower molar amount compared to the molar amount of a probe having a relatively low specific activity.

38. The method of claim 37, wherein each of the labeled probes comprises a chemiluminescent compound label selected from the group consisting of: standard acridinium ester (AE), naphthyl-AE, ortho-AE, 1- or 3-methyl-AE, 2-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE and 1- or 3-methyl-meta-difluoro-AE, provided that the different target-binding nucleic acids are each labeled with a different chemiluminescent compound.

39. The method of claim 32, wherein the incubating and measuring steps are performed in a single vessel.

40. The method of claim 32, wherein the contacting, incubating and measuring steps are performed in a single vessel.

41. A method for detecting an analyte in a sample comprising the steps of:

providing a probe reagent comprising two or more labeled probes, each of the labeled probes comprising a separately detectable label joined to a probe that specifically binds to a separate target region of an analyte, such that each labeled probe specifically binds to a target region that differs from that bound by another probe in the probe reagent and each separately detectable label is distinguishable from another separately detectable label in the probe reagent;

contacting
  i) a sample containing the analyte, and
  ii) the probe reagent, wherein each of the labeled probes is present in a predetermined molar amount sufficient to specifically bind to a predetermined amount of the analyte, and wherein the predetermined molar amount of each labeled probe differs from that of another labeled probe present in the probe reagent thereby allowing the probe reagent to detect the analyte over an extended concentration range that is greater than the concentration range of the analyte that is detected by one labeled probe present in the probe reagent;

incubating the sample and the probe reagent under conditions favoring specific binding of the labeled probes with the analyte, thereby forming at least one specific binding complex comprising at least one labeled probe and the analyte; and detecting at least one labeled probe present in the specific binding complex, thereby indicating that the analyte is present in the sample in a concentration range detected by the probe reagent.

42. The method of claim 41, wherein the contacting and incubating steps are preformed in a single vessel.

43. The method of claim 41, wherein the sample is not serially diluted before the contacting step.

44. The method of claim 41, wherein each of the labeled probes is labeled at a different specific activity of label such that a probe having a relatively high specific activity is present in a molar amount that is lower than a molar amount of a probe having a relatively low specific activity in the probe reagent.

* * * * *